Oct. 4, 1932. L. R. TAFT Plant Pat. 30

CHERRY

Filed March 16, 1932

Inventor:
L. R. TAFT
By Robb & Robb
Attorneys

Patented Oct. 4, 1932

Plant Pat. 30

UNITED STATES PATENT OFFICE

LEVI R. TAFT, OF EAST JORDAN, MICHIGAN, ASSIGNOR TO STARK BRO'S NURSERIES & ORCHARDS COMPANY, OF LOUISIANA, MISSOURI

CHERRY

Application filed March 16, 1932. Serial No. 599,299.

This discovery relates to a new and distinct variety of very early cherry, ripening with or slightly before the Early Richmond. Generally speaking, the tree in size and general shape is similar to the Montmorency variety, but is rather more stocky, with heavier branches, thicker leaves, having larger ribs and veins and slightly darker in color.

The fruit is larger than Early Richmond and has long rather heavy stems. In color it is quite unusual in that it is a deep, rich wine color. The juice is a deep red color, something like the English Morello and it is rather thick, but slightly less acid than the Montmorency.

The above description indicates that this new sour cherry is similar in type of tree and leaf to the Montmorency variety, but primarily distinguished therefrom by the different colored flesh and furthermore by the fact that it has at least ten days to two weeks earlier ripening season, corresponding to the ripening season of the Early Richmond, and that it has crimson flesh and lighter crimson juice, whereas the Montmorency has translucent flesh and juice. This early ripening of the same type of sour cherry as Montmorency, extends the cherry period over double the length of time and this, with the other advantages to be derived therefrom, well known to the trade.

In addition to the above distinctions, it may be noted that this new cherry is at least one third larger in size than the Early Richmond.

Figure 2:
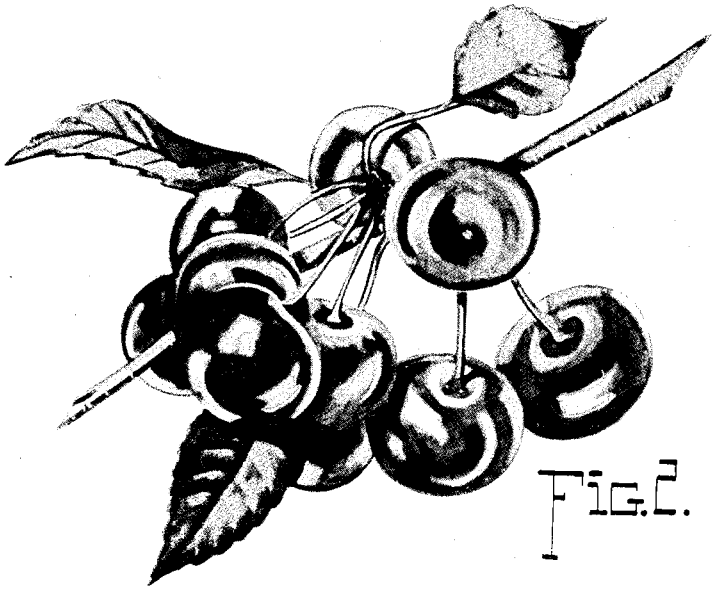
Fig. 2 is the new variety of cherry of this application at the Early Richmond ripe stage shown in Fig. 1, and Fig. 3, by comparison, the stage of ripening of the true Montmorency at the ripening stages of those shown in Figs. 1 and 2.
Figure 1:
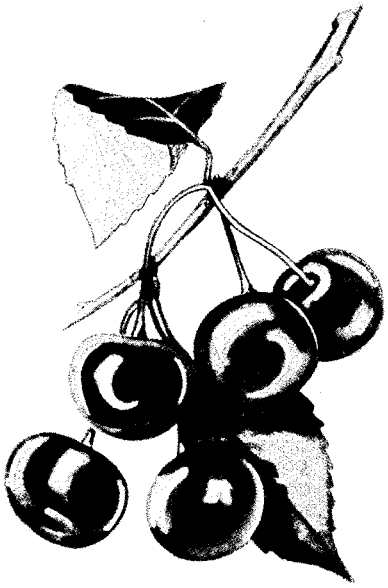
Fig. 1 represents the Early Richmond at its ripe stage.
Figure 3:
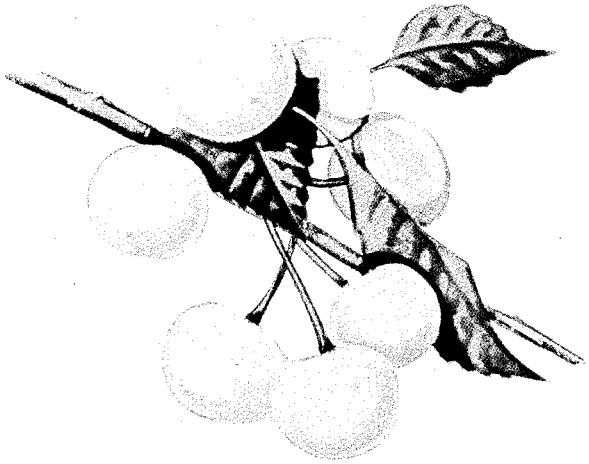

The following is a more detailed description of my new cherry:

*Leaves.*—Mature leaves on fruit spurs—size small to medium, 2½ inches long, 1½ inches wide. Form oval to slightly obovate. Texture rather heavy. Upper surface smooth, somewhat glossy, dark green. Lower surface smooth, but showing considerable whitish pubescence at the midribs and veins. Slightly lighter in color than the upper surface. Base broadly acute. Margin triple serrate. Serrations small. Apex pointed. Petiole rather long slender, 1¼ inches long. Glands small, often absent or situated on the base of the blade, rather large when fully developed, dark red in color.

*Fruit.*—Maturity very early with or slightly before Early Richmond. Size medium, axial diameter $\frac{11}{16}$ inch, large transverse diameter $\frac{13}{16}$ inch, smallest transverse diameter 12/16 inch. Form roundish oblate. Base medium with apex very slightly flattened. Stem fairly stout, medium length, 1 to 1⅛ inches with a noticeable collar or enlargement at the insertion. Cavity rather narrow, acute. Suture very faintly marked extending to the apex with the scar slightly indented. Skin very glossy with minute yellowish submerged dots scarcely noticeable. Color deep purplish crimson when fully mature. Skin thin, tough, separating from the flesh which is deep dull crimson, translucent with whitish veins easily traced. Juice abundant, color lighter than the flesh texture rather firm but tender and melting. Quality excellent.

*Seed.*—Stone medium size, separating readily from the flesh. Surface smooth except from distinct ridges on the dorsal suture. Color dull brown with a slight pinkish tinge. Form round oblique, sides unequal. Size ⅜ inch long, ⅜ inch wide, ¼ inch thick. Base broad, apex round. Ventral suture distinct but not prominent. Dorsal suture prominent with distinct ridges protruding to cause the oblique form.

I claim:

The cherry tree herein described, characterized by earliness of the ripening period of its fruit, as shown.

In testimony whereof, I affix my signature.

LEVI R. TAFT.